United States Patent [19]

Shoher et al.

[11] Patent Number: 5,014,532
[45] Date of Patent: May 14, 1991

[54] DENTAL SWAGER

[76] Inventors: Itzhak Shoher, 50 Shlomo-Hamelech St., Tel-Aviv, Israel, 64386; Aharon E. Whiteman, 13 J.L. Perez St., Petach-Tikvah, Israel, 49206

[21] Appl. No.: 445,923

[22] Filed: Dec. 4, 1989

Related U.S. Application Data

[63] Continuation of Ser. No. 190,066, May 4, 1988, abandoned.

[51] Int. Cl.$^5$ .............................................. B21D 22/10
[52] U.S. Cl. ...................................... 72/60; 433/223
[58] Field of Search ............... 433/218, 223; 72/57, 72/60, 465

[56] References Cited

U.S. PATENT DOCUMENTS

| | | | |
|---|---|---|---|
| 537,481 | 4/1895 | Parker | 72/60 |
| 906,911 | 12/1908 | McCullough | 72/57 |
| 950,294 | 2/1910 | Lothamer | 72/60 |
| 967,873 | 8/1910 | Franke | 72/60 |
| 1,044,892 | 11/1912 | Lamb | 72/60 |
| 1,794,197 | 2/1931 | Montuori | 72/60 |
| 1,883,968 | 10/1932 | Krivig | 72/60 |
| 2,368,717 | 2/1945 | Marschner | 72/60 |
| 2,738,575 | 3/1956 | Swain et al. | 72/465 |
| 2,841,083 | 7/1938 | Kirkpatrick et al. | 72/57 |
| 4,162,625 | 7/1979 | Simmons | 433/34 |
| 4,689,979 | 9/1987 | Otsuka et al. | 72/465 |

FOREIGN PATENT DOCUMENTS

| | | | |
|---|---|---|---|
| 3447841 | 7/1986 | Fed. Rep. of Germany. | |
| 8601717 | 2/1987 | Fed. Rep. of Germany. | |
| 0835610 | 12/1938 | France | 433/218 |
| 0660754 | 5/1979 | U.S.S.R. | 72/465 |

*Primary Examiner*—John G. Weiss
*Assistant Examiner*—Adriene B. Lepiane

[57] ABSTRACT

A dental swager for adapting a dental foil coping to a die of the tooth to be restored, comprising a male punch and a female base support in which the die of the tooth to be restored is mounted with the foil coping placed over the die. An insert is located in the male punch for transferring the force applied to the punch to the coping and die. The insert is composed of a solid material having an elastic memory. A shock absorber having a putty-like consistency separates the insert from the male punch.

3 Claims, 1 Drawing Sheet

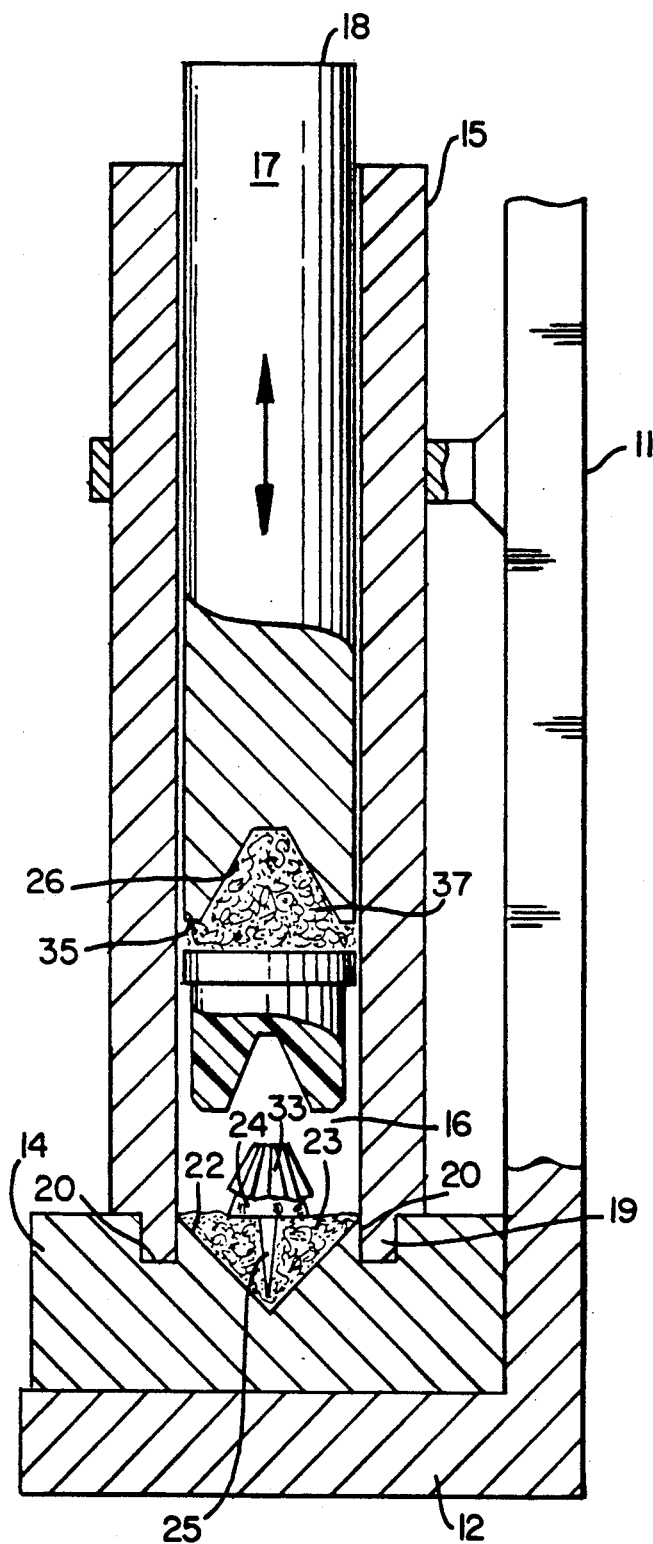
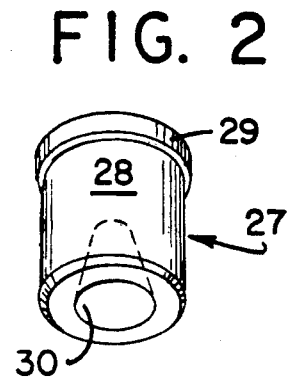
FIG. 2
FIG. 1

DENTAL SWAGER

This application is a Continuation of prior U.S. application Ser. No. 190066 Filing Date 05/04/88 abandoned.

FIELD OF INVENTION

This invention relates to a dental swaging device for adaptation of a dental foil coping to a die.

BACKGROUND OF THE INVENTION

A relatively new technique for constructing a ceramic to metal crown from a foil coping is disclosed in U.S. Pat. Nos. 4,459,112 and 4,492,579, respectively. The foil coping is formed from a thin metal foil starting material, preferably in the form of a laminate of precious metal layers with a composite thickness of between 15-100 mils. The foil is prefolded into a geometrical form having a plurality of foldable sections which extend radially from a central, preferably unfolded central area. In the preferred embodiment, the foldable sections form pleats which overlap each other when folded over. The recommended procedure for forming the coping from the foil is to place the geometric form over the die of the tooth to be restored and to fold over each section in sequence, either clockwise or counter-clockwise. Each folded section may also be burnished to remove any trapped air spaces and to tightly engage the folds to the die in an overlapping relationship. After burnishing the foil is ready to be swaged. The swaging operation more accurately adapts the foil to the die to form a coping which replicates the shape of the die.

Dental swaging devices are not new. Fundamentally, the swaging instrument consists of a female die and a male punch. The die of the tooth to be restored is mounted in the female die. A metal form such as a foil coping is mounted over the die in alignment with the male punch. The male punch is then struck repeatedly with a hammer or mallet until the form is compressed into adaptation against the die.

Since the die of the tooth is composed of ceramic or other fragile composition and since the metal coping is also relatively thin, it has heretofore been necessary to incorporate highly viscous plastic compound such as clay in a putty-like consistency into the swaging device between the male punch and the die to protect the foil coping from tearing and to prevent damage to the die. After each use of the swager, the foil coping must be removed from the putty-like compound, which is not only a very time-consuming operation but is also impractical. Moreover, although the putty-like compound protects the foil coping and the die of the tooth, it requires the operator to consistently hit the male punch many times over and with substantial force. Accordingly, it is difficult to assure reproducible quality.

It is therefore the principal object of the present invention to provide a dental swager which overcomes all of the disadvantages of conventional dental swagers.

SUMMARY OF THE INVENTION

The dental swager of the present invention comprises a base member for supporting a die of the tooth to be restored, a male punch having a piston reciprocally mounted in an elongated chamber vertically extending above said die, and a solid insert mounted in said chamber below said piston and in alignment therewith for engaging said die upon applying a vertically downward force to said piston, with said insert being composed of a solid material having an elastic memory and having an indentation facing said die with a shape in substantial conformity to the shape of the die.

BRIEF DESCRIPTION OF THE DRAWINGS

Other objects and advantages of the present invention will become apparent from the following detailed description of the invention when read in conjunction with the accompanying drawings of which:

FIG. 1 is a side elevation of the dental swager of the present invention in cross section; and FIG. 2 is a perspective view of the insert shown in FIG. 1.

DETAILED DESCRIPTION OF THE PREFERRED EMBODIMENT

The swaging device (10) of the present invention is diagrammatically shown in FIG. 1, comprising a framework including a vertical stand (11), a foot (12) horizontally extending from the vertical stand (11), a metal base (14) mounted upon the foot (12), and a male punch (15) connected to the vertical stand (11). The male punch (15) is a cylindrical member having a chamber (16) and a piston (17) reciprocally mounted within the chamber (16) for vertical movement in response to a vertical force applied to the top end (18) of the piston (17). The force applied to the piston (17) may be applied by impact from any conventional device such as a hammer or mallet, or may be a varying pressure force. The male punch (15) has a depending collar (19) which removably fits into a slot (20) formed in the metal base (14).

The metal base (14) has a depression (22) filled with a viscous putty-like compound, such as clay, (23) for supporting a female die (24) of the tooth to be restored. The geometry of the depression (22) is not critical to the invention, although it should be deeper than the pin (25) extending from the die (24). The pin (25) is immersed into the compound (23) leaving the die (24) on a plane level with the base (14).

A removable insert (27) is mounted in the chamber (16) below the bottom end (26) of the piston (17). The insert (27) has a body (28) and a larger diameter annular shoulder (29), preferably at the end adjacent the piston (17). The shoulder (29) contacts the chamber wall for movement in a vertical direction in response to movement of the piston (17). The removable insert (27) transfers the force delivered from the piston (17) to the die. The insert (27) is composed of a solid, resilient material having an elastic memory, preferably of a silicone composition. Silicone is preferred not only because it has an elastic memory but also because it will not stick to the die regardless of the force applied to the piston (17).

The characteristic of a solid, resilient material having an elastic memory is critical to the function of the insert (27). The insert (27) has an indentation (30), preferably shaped to match the contour of the die (24) or in general conformity therewith. Accordingly, when a metal foil (33) is placed on the die (24) and the piston (17) is struck with a hammer, the force delivered to the insert (27) forces the metal foil (33) to adapt to the shape of the die (24). When the force applied to the piston (17) is lifted, the insert (27), due to its elastic memory, will substantially restore itself to its normal unstressed shape, preventing residual distortion in the insert from distorting the foil (33). The insert (27) also separates itself from the die (24), which minimizes distortion upon removal of the coping from the die.

To prevent the piston (17) from bouncing and vibrating, particularly from a sudden impact force, a shock absorbing material (37) such as a clay, may desirably be interposed between the insert (27) and the bottom end (26) of the piston (17). The bottom end (26) of the piston (17) may also be shaped so that only the surface area (35) around the circumference at the bottom end (26) will strike the insert (27). This assures a more uniform transfer of the force applied to the piston (17) and less likelihood of misalignment.

Although the insert (27) is preferably of silicone, any solid, resilient, plastic material having an elastic memory may be used. For purposes of this invention, an elastic memory is characterized by a material which is sufficiently resilient to permit it to deform under the application of pressure, but has an elastic or elasto-plastic capability so that upon removal of the pressure it will substantially return to its original non-deformed shape. This assists separation of the insert from the die and prevents distortion. The insert (27) is preferably a single member, although a composite of several members co-acting as one may be used.

What we claim is:

1. A dental swager for adapting a metal coping to a dental die comprising:

a base member for supporting the die of the tooth to be restored with said coping adapted to be placed over said die;

a male punch having a piston reciprocally mounted in an elongated cylinder vertically extending above said die with said piston having a top end extending from said cylinder for being hit by a hammer; a removable solid insert slidably mounted in said cylinder below said piston and in alignment therewith for engaging said die upon hitting said top end of said piston with such hammer; and shock absorber means having a putty-like consistency for separating said insert from said piston wherein said insert is composed of a solid, resilient material having an elastic memory and an indentation facing said die with the indentation having a shape in substantial conformity to the shape of the die for striking the metal coping.

2. A dental swager as defined in claim 1, wherein said insert is composed of silicone.

3. A dental swager, as defined in claim 2, wherein said insert has a cylindrical body and a protruding head of larger diameter than the body, with the diameter of the head being substantially equal to the diameter of said cylinder.

* * * * *